(12) United States Patent
Steiner et al.

(10) Patent No.: US 8,152,808 B2
(45) Date of Patent: Apr. 10, 2012

(54) SURGICAL BONE CUTTING ASSEMBLY AND METHOD OF USING SAME

(75) Inventors: Anton J. Steiner, Warton, NJ (US);
David I. Knight, Perth Amboy, NJ (US);
Paul J. Mulhauser, New York, NY (US); Karl D. Kirk, III, New York, NY (US); Richard J. Cosenza, Island Park, NY (US); Gregory C. Fanelli, Danville, PA (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 403 days.

(21) Appl. No.: 12/453,998

(22) Filed: May 28, 2009

(65) Prior Publication Data
US 2009/0299371 A1 Dec. 3, 2009

Related U.S. Application Data

(60) Provisional application No. 61/129,028, filed on May 30, 2008.

(51) Int. Cl.
*A61B 17/00* (2006.01)
(52) U.S. Cl. ........................................... 606/79
(58) Field of Classification Search ............. 606/79–102
See application file for complete search history.

(56) References Cited

U.S. PATENT DOCUMENTS

| | | | |
|---|---|---|---|
| 5,919,196 A | 7/1999 | Bobic et al. | |
| 6,488,033 B1 | 12/2002 | Cerundulo | |
| 6,591,581 B2 | 7/2003 | Schmieding | |
| 6,592,588 B1 | 7/2003 | Bobic et al. | |
| 6,699,252 B2 * | 3/2004 | Farr et al. | 606/79 |
| 6,852,114 B2 | 2/2005 | Cerundolo | |
| 2003/0114859 A1 * | 6/2003 | Grusin et al. | 606/87 |
| 2007/0021838 A1 * | 1/2007 | Dugas et al. | 623/20.3 |
| 2009/0192516 A1 * | 7/2009 | Tallarida et al. | 606/96 |

* cited by examiner

*Primary Examiner* — Suzette J Gherbi
(74) *Attorney, Agent, or Firm* — John S. Hale; Gipple & Hale

(57) ABSTRACT

The invention is directed toward a surgical kit having component parts capable of use in excising a cartilage defect site on a patient to prepare the same for receipt of an implant plug, the kit comprising a cylindrical gauge with a central bore used to measure the defect area, a guide rod adapted to be driven through the gauge tube into the center of said defect area and a cartilage cutting assembly adapted to be mounted over the guide rod and used for excising the defect area and cutting a cylindrical bore into the defect area. The method for use of the kit comprises the steps of: marking the defect area to be cut; placing a guide rod into the center defect area and driving the same to a predetermined distance to secure the same in the defect area and placing a drill bit over the guide rod and rotating the drill bit to cut a cylindrical blind bore removing the cartilage defect.

20 Claims, 16 Drawing Sheets

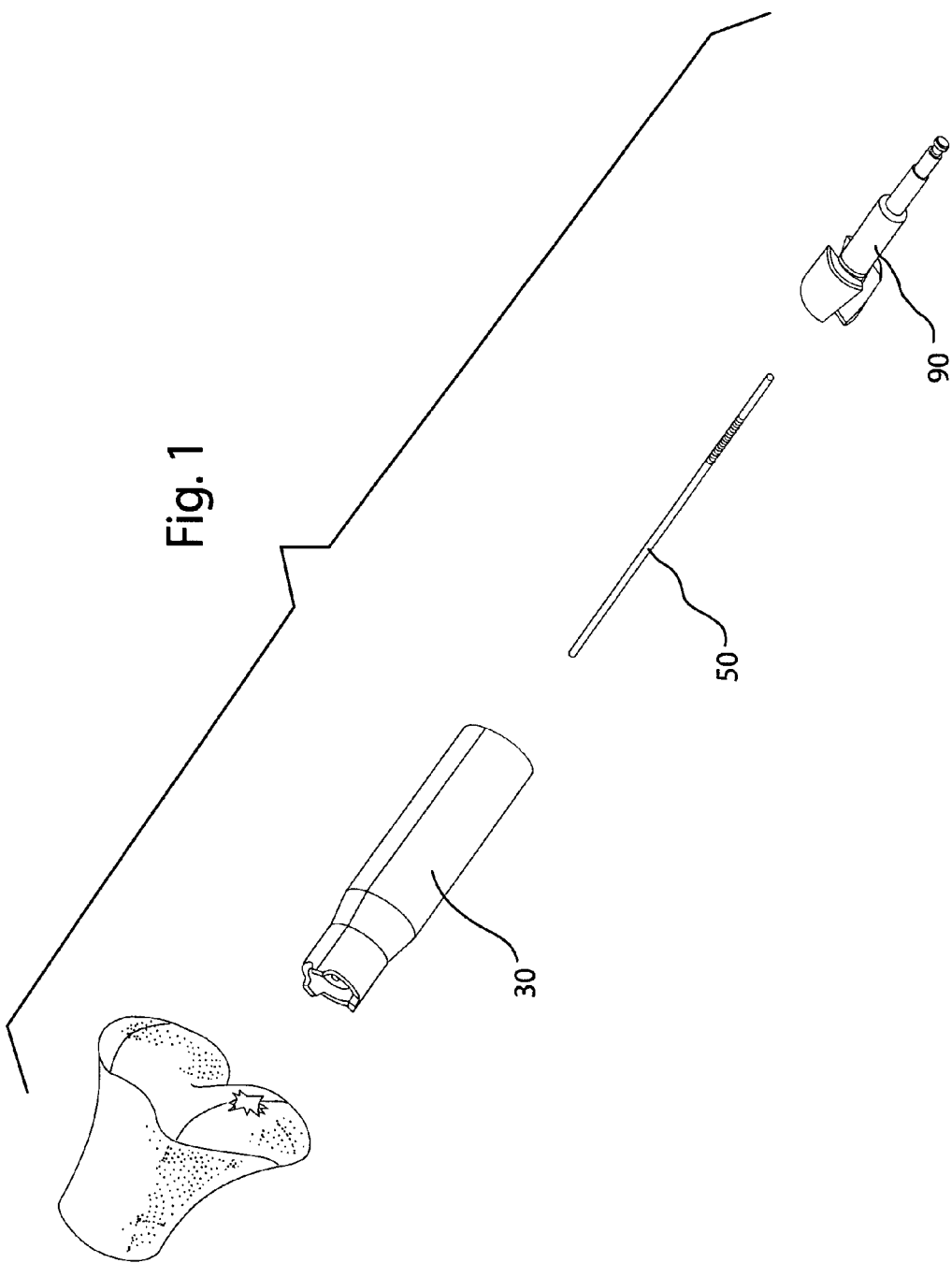

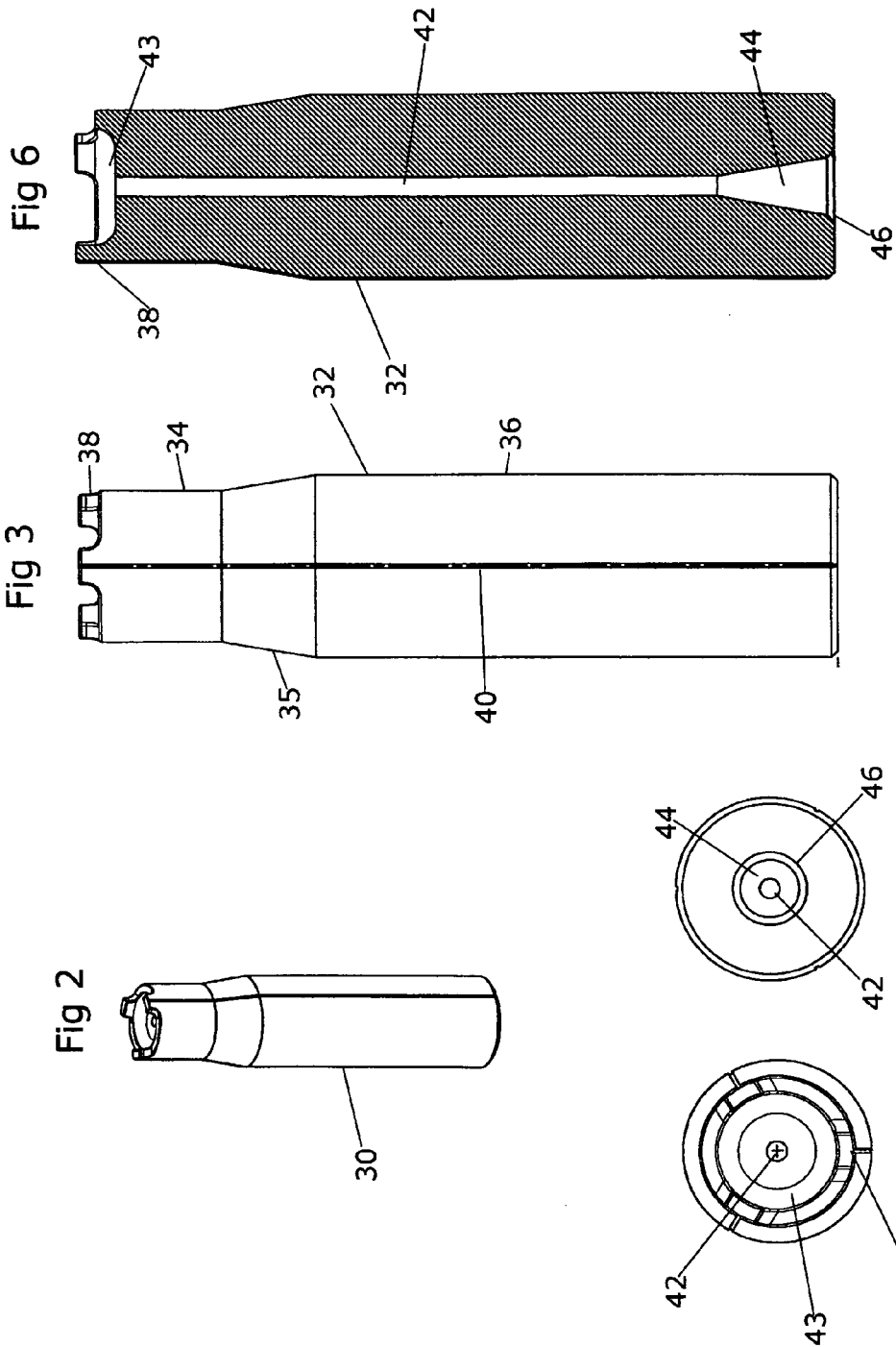

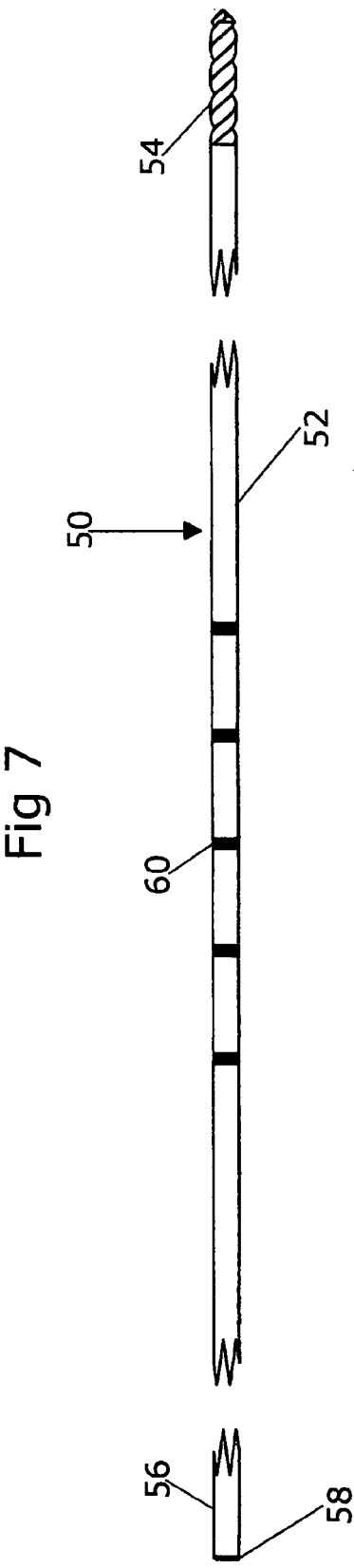

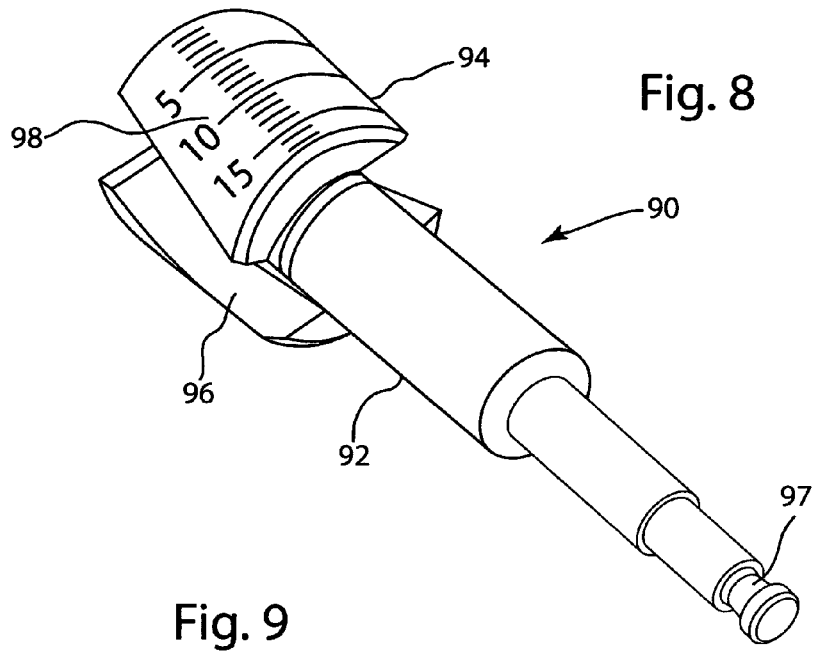
Fig. 8
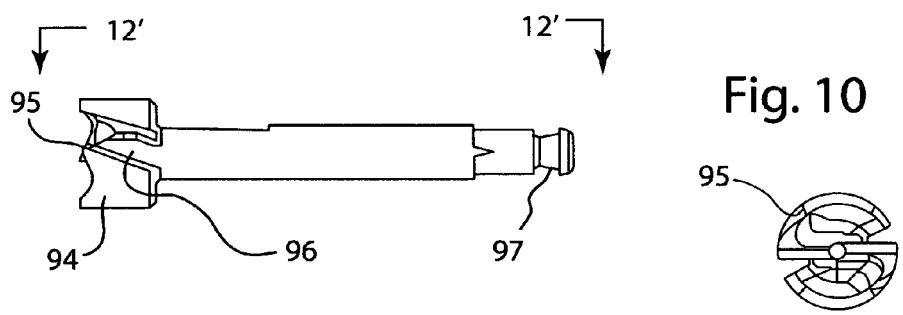
Fig. 9
Fig. 10
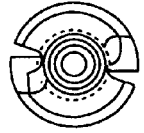
Fig. 11
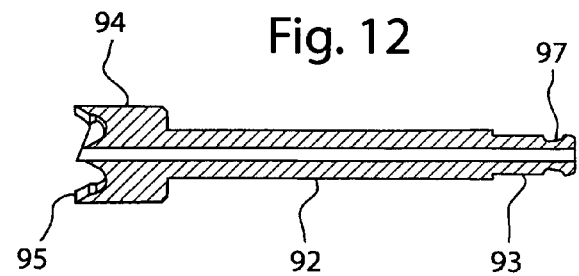
Fig. 12

SURGICAL BONE CUTTING ASSEMBLY AND METHOD OF USING SAME

RELATED APPLICATIONS

The present application is related to and claims priority from U.S. Provisional Patent Application No. 61/129,028 filed May 30, 2008.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention is generally directed toward the surgical treatment of articular chondral defects and is more specifically directed toward a surgical cutting assembly for removing the cartilage defect from the patient by drilling a blind bore in the defect area ranging from 10 to 40 mm in diameter to excise the defect area allowing a cylindrical allograft cartilage implant plug to be accurately orientated and placed in the blind bore.

2. Description of the Prior Art

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of an extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the cartilage lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. Patient or recipient repair sites are normally present in the weight bearing area of the medial and lateral femoral condyles. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age have obtained good clinical results, which most likely reflects the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. Carticel® is a commercial process to culture a patient's own cartilage cells for use in the repair of cartilage defects in the femoral condyle and is marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with cambium layer is sutured around the defect and is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The autologous osteochondral plugs are harvested from a lower weight-bearing area of lesser importance in the same joint. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts also carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of United States patents have been specifically directed towards the manufacture of plugs or cores which are implanted into a cartilage defect. U.S. Pat. No. 6,591,581 issued Jul. 15, 2003 describes a precut bone plug for use in allograft core transplantation surgery which has a tissue bank harvest the graft using a coring trephine with teeth having an inner diameter between 0.5 mm to 0.1 to create a bone core with a hyaline cartilage layer in approximately 7.9 mm, 9.9 mm, 11.9 mm diameters. A donor cutting harvester having a cutter tube with a straight cutting edge, a window slot and depth markings with a torque handle on the proximal end may be used to obtain an autograft core as is shown in U.S. Pat. No. 5,919,196 issued Jul. 6, 1999. This same reference also discloses a punch cutter which is cannular. As noted in U.S. Pat. No. 6,591,581 issued Jul. 15, 2003 an allograft osteochondral transplantation method is known, in which a surgeon is provided with a whole cadaver knee from a tissue bank along with an instrument set containing the full range of sizers and sized instruments. In this allograft method, the surgeon must determine the size for the graft needed and then perform the surgery. The '581 patent notes that this method is undesirable due to several factors including the preoperative preparation required for the surgeon to harvest and prepare the donor core, the waste from discarding each cadaver knee after the one operation without realizing the full potential for each knee to yield multiple allograft cores and the comprehensive instrumentation system which must be sent to and recovered from the operation site. This patent discloses instruments for cutting a bone core by cutting or punching having collared pins disposed within the harvester for removal of the harvester cores. U.S. Pat. No. 6,592,588 issued Jul. 15, 2003 discloses apparatus for allograft transplantation of articular cartilage with bone from one site to another to treat chondral defects. The '588 patent discloses a handle having a cylindrical bar extending through it transverse to the axis of the cutting tube mounted to the handle. The cutting tube is provided with a longitudinal slot which allows view of the depth of the penetration of the cutting tube.

U.S. Pat. Nos. 6,488,033 and 6,852,114 (a divisional application of the '033 patent) issued respectively Dec. 3, 2002 and Feb. 8, 2005 are directed toward an osteochondral transplant workstation for cutting a core out of an allograft bone held in an adjustable vise with a lubricated rotary cutting bit. The core is removed from the bit, held in a specially designed set of pliers, and cut to size by a saw blade to fit into a blind bore which has been oriented and drilled into the patient's arthritic defect area. This workstation while an improvement over existing procedures is cumbersome to use and requires experience and training.

The present invention was designed to overcome prior art procedures and provide a simple to use bore cutting assembly which accurately excises the patient's bone defect area to form a clean cut bore in the patient for receipt of the core shaped implant.

SUMMARY OF THE INVENTION

A surgical kit having component parts capable of use in excising a cartilage defect site in a patient to prepare the same for receipt of an implant plug, the kit comprising; a sizing gauge used to accurately measure the defect area, the gauge defining a bore which holds and guides a guide drill rod. The guide drill rod is adapted to be driven into the center of said defect area and extend therefrom and a cartilage cutting assembly is adapted to be mounted over the guide drill rod. The cartilage cutting assembly comprises a drill bit with a cannula adapted to be mounted over the guide drill rod for excising the defect area and cutting a cylindrical bore into a patient's condyle.

The method for use of the cutting assembly comprises the steps of: a) marking the defect area to be cut with a sizer gauge; b) placing a guide rod into the sizer gauge and driving the guide rod in the defect area a predetermined distance to secure the guide rod in the defect area; c) inserting a cutter assembly over the guide rod onto the defect area and cutting the cartilage around the defect area and cutting a cylindrical blind bore removing the defect area.

It is an object of the invention to provide a surgical kit for forming a cleanly cut bore with a sharply cut cartilage layer of the correct diameter size for the insertion of an allograft plug to repair a cartilage defect.

It is also an object of the invention to provide a surgical kit allowing the excision of the defect area for cartilage repair.

It is yet another object of the invention to provide a surgical kit having a cutter which scores the cartilage area prior to cutting and excising the cartilage defect site.

It is still another object of the invention to provide a surgical kit which marks and defines the defect area to be excised.

It is further an object of the invention to provide a surgical kit which can be easily used by the surgeon to create a correctly dimensioned blind bore.

It is yet another object of the invention to provide a surgical kit which can be easily cleaned and sterilized with disposable parts which can be discarded after the one use.

It is still another object of the invention to provide a kit to allow accurate bore diameter selections and depths.

It is a further object of the invention to provide a surgical kit which allows the cartilage layer to be removed without cracking or breaking the surrounding remaining cartilage layer.

These and other objects, advantages, and novel features of the present invention will become apparent when considered with the teachings contained in the detailed disclosure along with the accompanying drawings.

BRIEF DESCRIPTION OF THE DRAWINGS

FIG. 1 is an exploded perspective view of the inventive cartilage defect cutting assembly;
FIG. 2 is a perspective view of the lesion gauge shown in FIG. 1;
FIG. 3 is an enlarged side elevation view of the lesion gauge shown in FIG. 2;
FIG. 4 is a top plan view of the distal end of the lesion gauge shown in FIG. 3;
FIG. 5 is a bottom plan view of the proximal end of the lesion gauge shown in FIG. 3;
FIG. 6 is a cross section of FIG. 3 taken along line 6'-6';
FIG. 7 is an enlarged exploded side view of the guide rod shown in FIG. 1;
FIG. 8 is an enlarged perspective view of the cannular cutting reamer shown in FIG. 1;
FIG. 9 is a reduced side view of the cannular cutting reamer shown in FIG. 8;
FIG. 10 is a front view of the distal end of the cannular cutting reamer shown in FIG. 9;
FIG. 11 is a rear elevational view of the proximal end of the cannular cutting reamer shown in FIG. 9;
FIG. 12 is a cross sectional view of FIG. 10 taken along line 12'-12'.

DESCRIPTION OF THE INVENTION

Figure 13:
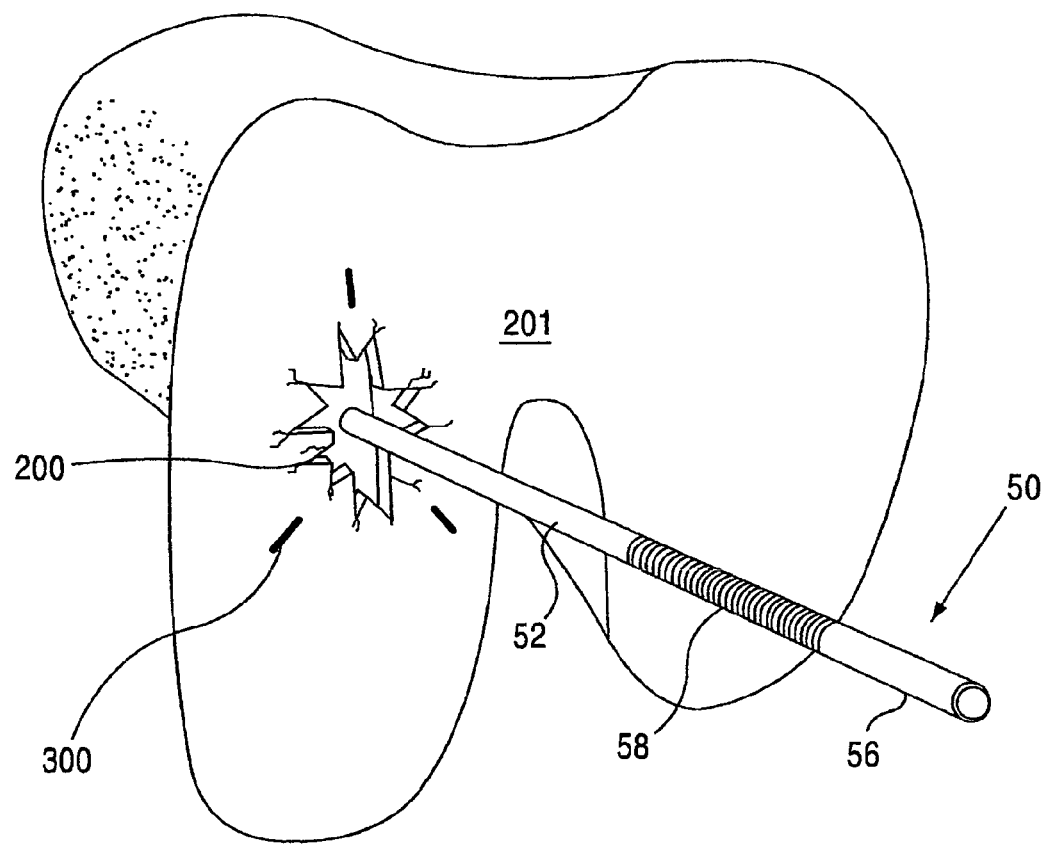
FIG. 13 is a perspective view showing the marked area around the defect and the guide rod extending from the defect area of the condyle.
Figure 14:
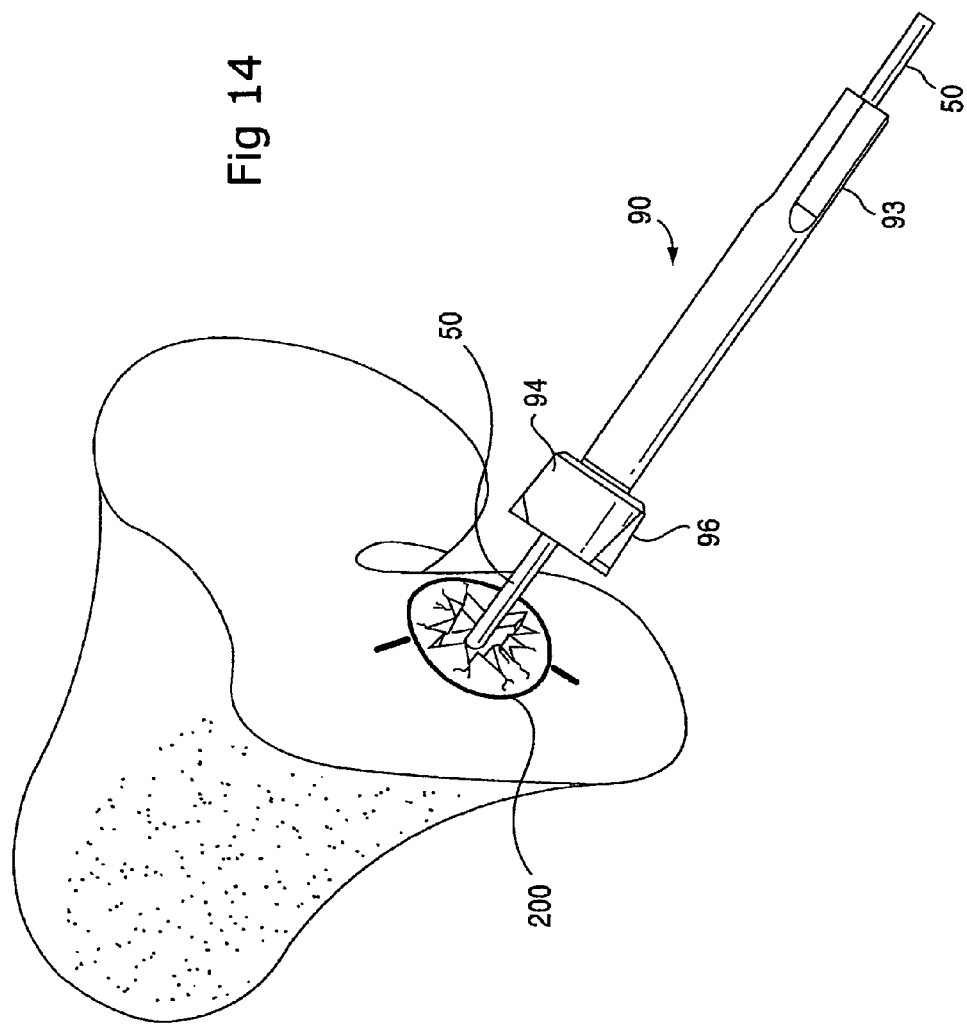
FIG. 14 is an enlarged perspective view of a cannular cutting reamer shown in FIG. 1 mounted on the guide rod for boring.

The term "tissue" is used in the general sense herein to mean any transplantable or implantable tissue such as bone.

The terms "transplant" and "implant" are used interchangeably to refer to tissue (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to tissue which originate with or are derived from a donor of the same species as the recipient. The terms "xenogeneic" and "xenograft" refer to tissue which originates with or are derived from a species other than that of the recipient.

The present invention is directed towards a cartilage cutting kit or assembly 20 as seen in FIG. 1 for cutting a circular area to remove a cartilage defect 200. The preferred embodiment and best mode of the invention is shown in FIGS. 1-14.

In the preferred embodiment of the cartilage cutting kit 20, a cartilage lesion gauge 30 is used to mark the area around the defect area 200 and orient the drill rod 50 so that it can be driven into the defect area. The lesion gauge 30 as best seen in FIGS. 2-6 is placed over the cartilage defect area 200 so that the defect area is covered. It will be appreciated that the gauge is substantially cylindrical and can have different sized diameters ranging from 10, 15, 18, 20, 22, 25, 30 and 35 mm. Furthermore each kit comes with a number of different sized (diameter) gauges to allow the covering of cartilage defect areas of different sizes. The gauge body 32 has a solid one piece construction with cylindrical distal or front section 34, a tapered or conical middle section 35 and a larger diameter proximal or rear section 36. The material forming the body is preferably color coded in different colors representing the different diameters of the gauge body 32. The distal end section 34 of the gauge body 32 is formed with extending tripod legs 38 and a linear sighting channel 40 cut in the exterior surface of the body runs from the proximal end of the body to the bottom of each leg 38 to form a sighting line for the surgeon as can be seen in FIG. 3. A throughgoing bore 42 is cut through the center of the body 32 to receive a guide drill rod 50. The bore 42 widens at its proximal end in a funnel or cone shape 44 with a chamfered edge 46 which allows easy insertion of the guide drill rod 50 during surgery. The distal end of bore 42 communicates with a cup shaped recess 43 cut into the distal end of the body section 34.

An appropriate sized body (diameter) 32 is selected and placed in a three point stance on the condyle cartilage surface 201 surrounding the defect area 200 and alignment marks 300 are drawn on the cartilage surface 201 around the patients cartilage defect area 200. The tripod leg structure of the body offers greater stability on the slippery condyle cartilage surface. The orientation of the tripod legs assure correlation of alignment of the allograft core to the patient's defect bore. The surgeon selects an appropriately sized gauge to cover the lesion which also determines the size of the reamer bit. It will be appreciated that a number of reamer bits having corresponding diameters to those of the lesion gauges are also provided in the kit. The patients defect site is marked at 12 o'clock and at approximately 4 and 8 o'clock if the surgeon so chooses. The 12 o'clock position is critical. The same marking are placed on the osteochrondal core created from the allograft. Once the defect site 200 has been sized by the lesion gauge 30, a guide rod 50 is drilled through the cannulated lesion gauge 30 to maintain a point of reference allowing the guide rod 50 to be positioned perpendicular to the defect 200.

The guide rod 50 as seen in FIG. 7 is constructed with a shaft 52 having a drill screw tip 54 at its distal end and a smooth surface 56 with a chamfer 58 or chuck at its proximal end. Drill depth markings 60 are provided on the shaft 52 to allow visualization of the drill depth. Once the guide drill rod 50 is driven into the defect area 200 and the lesion gauge 30 is removed the drill rod 50 extends outward from the defect area 200.

The lesion gauge 30 is slid off the guide rod 50 and a reamer bit 90 is placed over the guide rod 30 for removal of the defect and creation of the blind bore. The reamer bit 90 is designed so that its cutting blades score the cartilage surface first and then cut through the cartilage and subchrondal bone.

Figure 15:
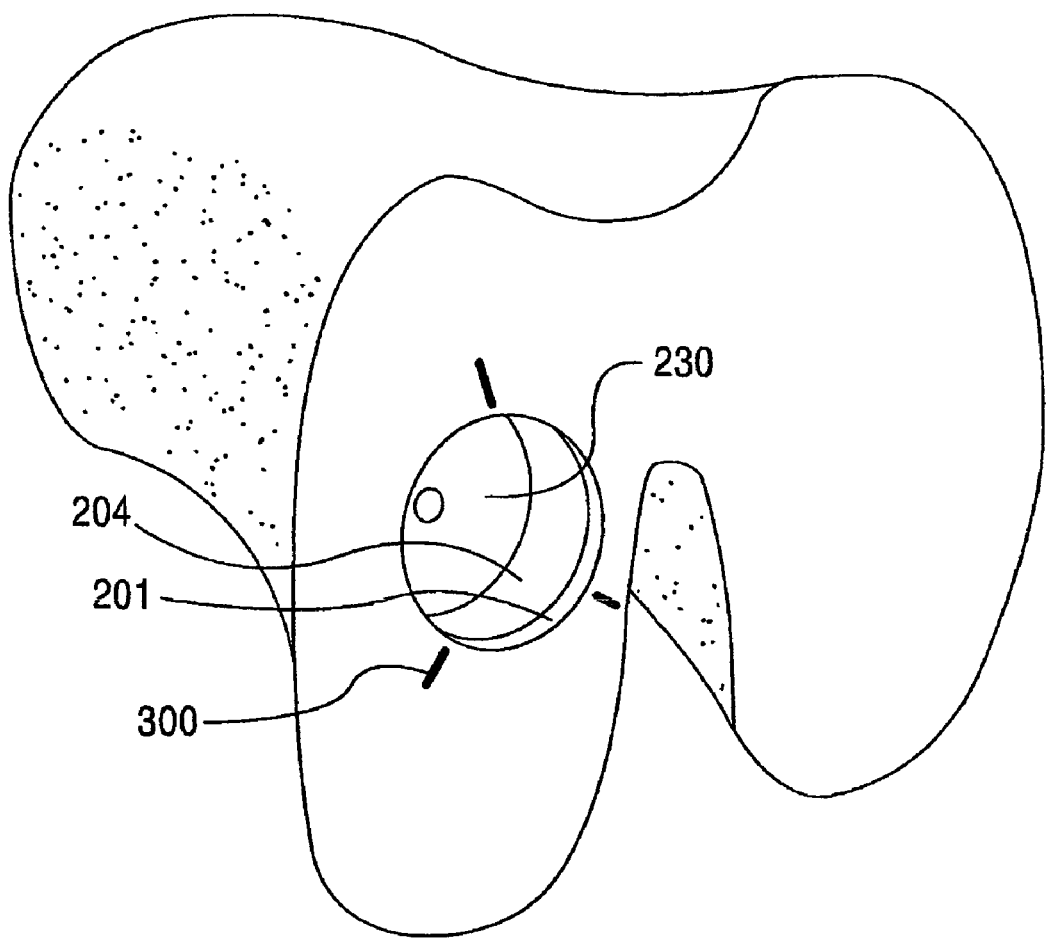
FIG. 15 is a perspective view of the medial condyle surface with the blind bore cut through the cartilage layer and cortical bone layer into the cancellous bone of the defect site forming a prepared recipient site.

The reamer cutting or boring bit 90 has a cannular shaft 92 with a cutting blade 94 as seen in FIGS. 8, 9 and 12 and a stepped chuck 93 with a Hudson quick disconnect 97 on the proximal end. The cutting blade 94 has a sharp leading edge 95 to initially score the cartilage and keep the cartilage from chipping during the initial cartilage cutting and has a second edge for cutting the bone and defines two angled channels 96 to direct the cut cartilage and bone shard materials upward through the bit and outside of the bore. The reamer bit 90 is marked with laser bore depth markings 98 so that the depth of the bore 230 can be easily and accurately determined. The cutting blade 94 is driven by a standard drill and the cutting action results in a clean blind bore 230 cut into the patient as seen in FIG. 15. The reamer bit 90 is removed from the guide rod 50. A depth gauge (not shown) is placed on the guide rod 50 and slid into the bore to measure the depth of the blind bore 230 at the three locations of 12, 4 and 8 o'clock as previously noted. The depth gauge is removed from the guide rod 50 and a dilator is placed over the guide rod 50 and driven into the blind bore 230 to slightly expand same prior to insertion of the osteochrondal plug.

Figure 16:
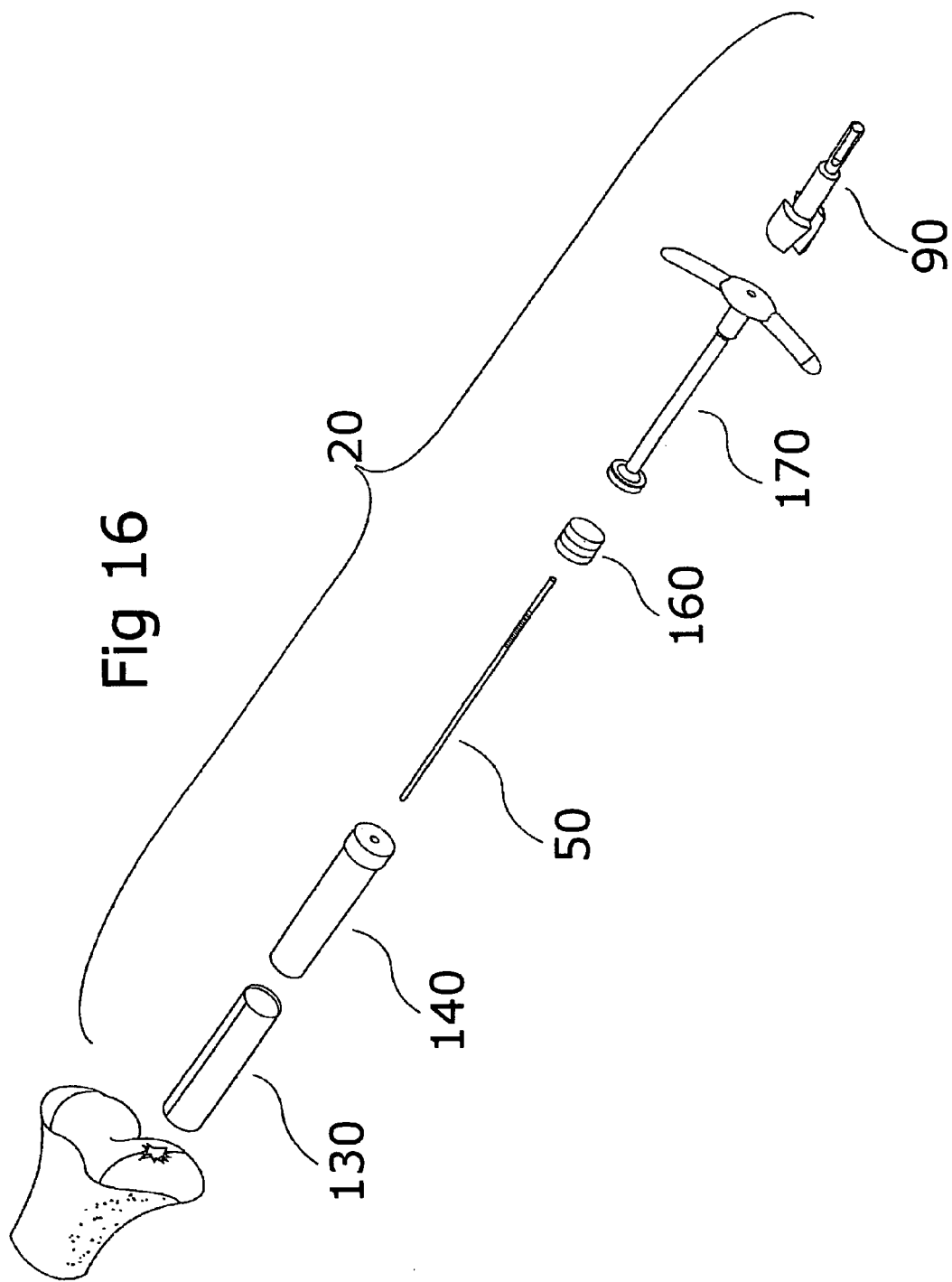
FIG. 16 is an exploded perspective view of an alternative embodiment of the cartilage defect cutting assembly.
Figure 17:
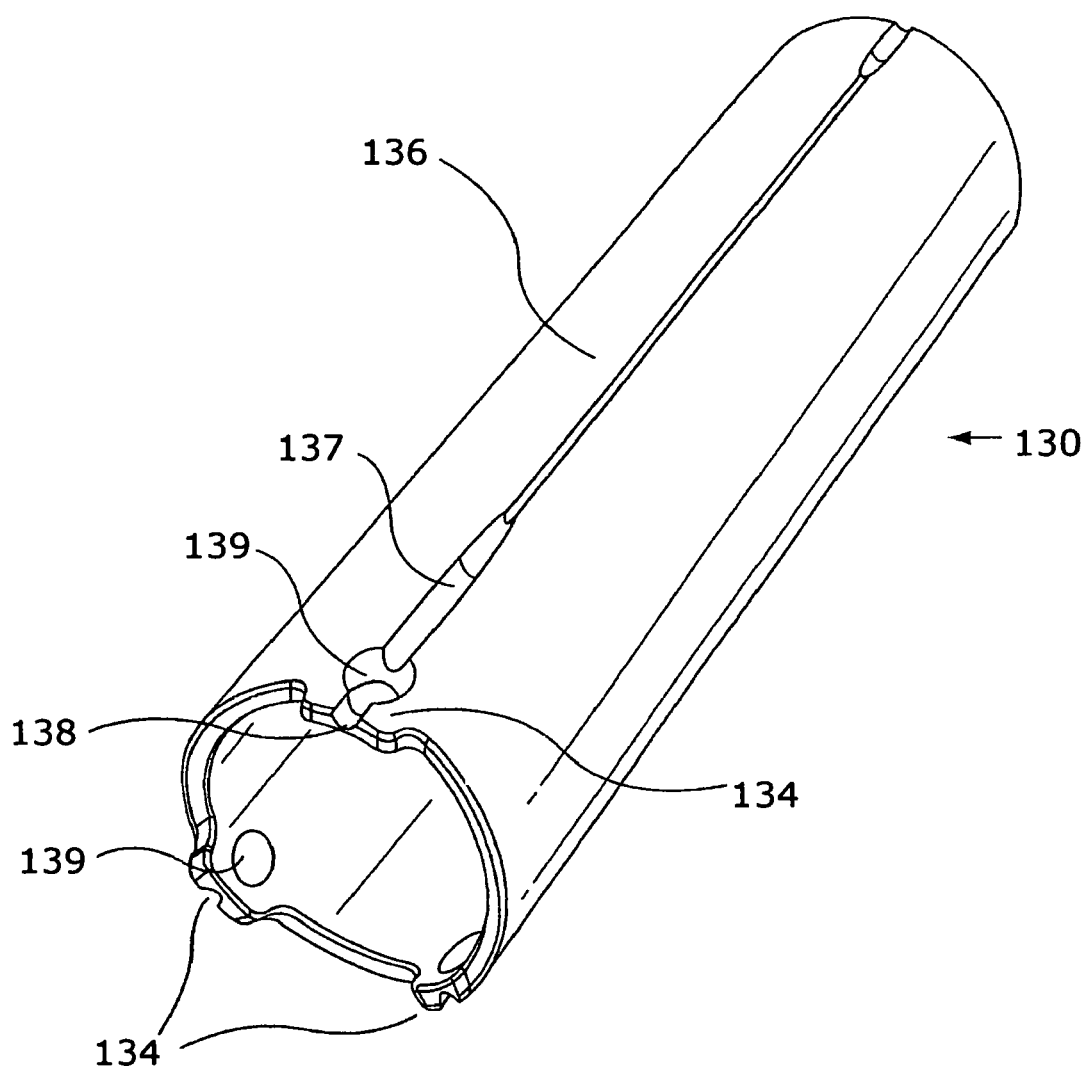
FIG. 17 is an enlarged perspective view of the sizing tube shown in FIG. 16.
Figure 18:
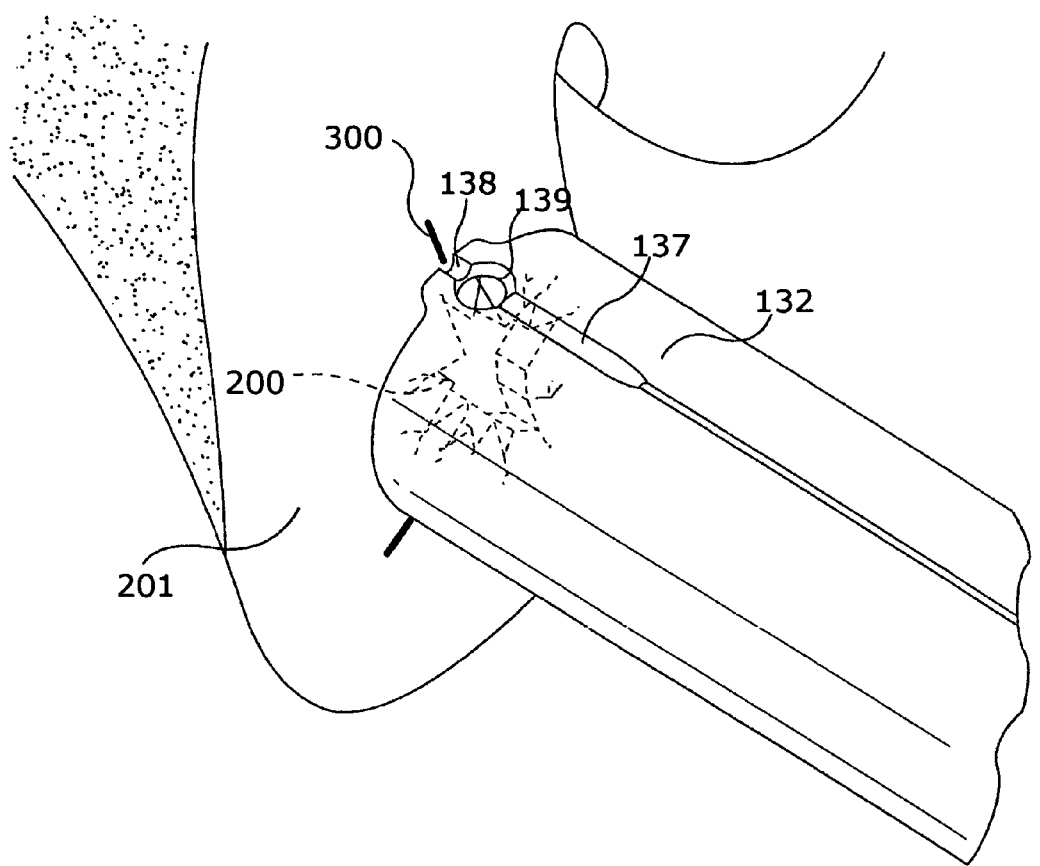
FIG. 18 is a partial view of the distal end of the sizing tube shown in FIG. 17 placed on a condyle with a defect.
Figure 19:
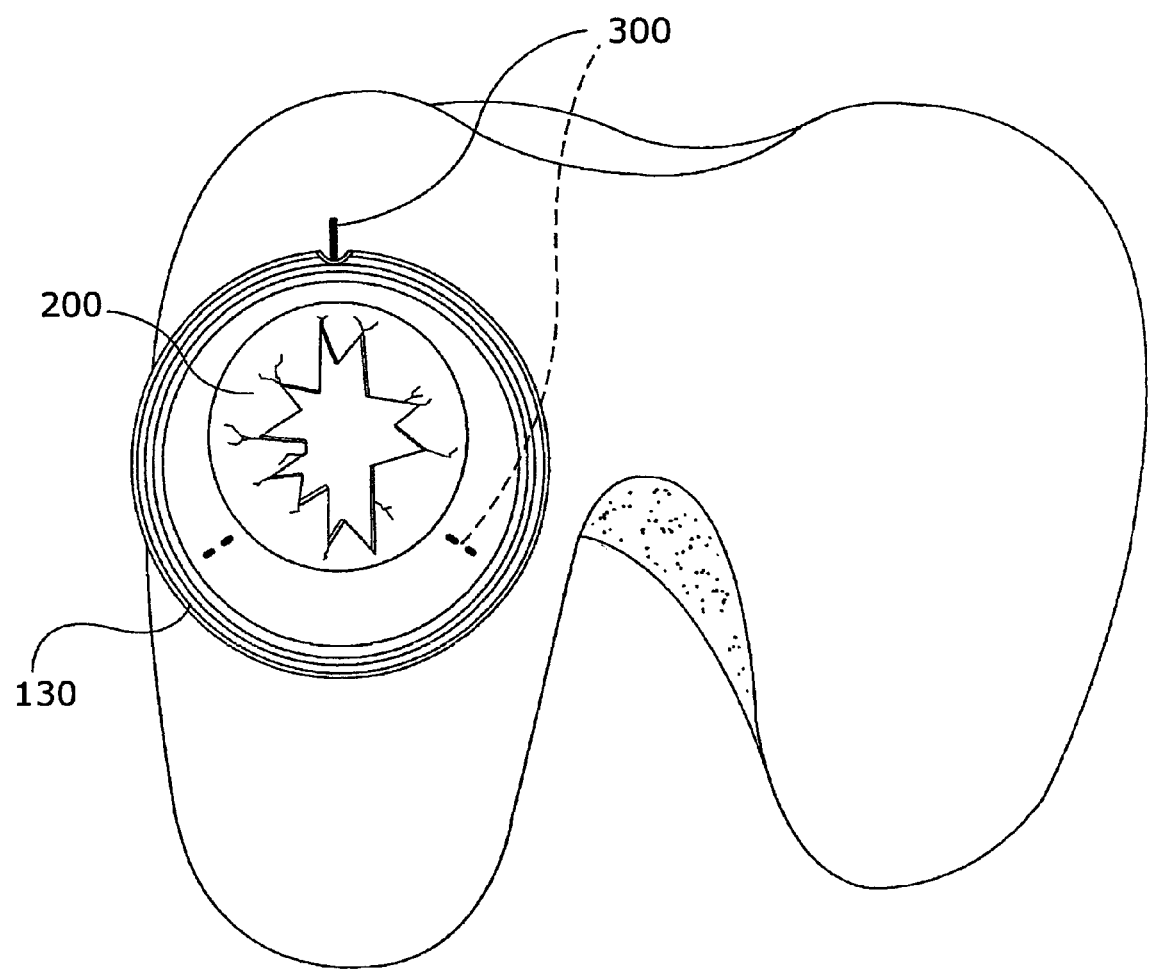
FIG. 19 is an end view of the sizing tube shown in FIG. 17 looking down on the defect area.

An alternative embodiment of the cartilage cutting assembly 120 is seen in FIG. 16. In this embodiment a sizing tube 130 as seen in FIGS. 17 and 18 is used to measure the defect area 200. The sizing tube 130 is a cylindrical body 132 made of transparent plastic for maximum visualization of the defect or of anodized aluminum which is color coded for quick size matching. It will be appreciated that different diameter sizing tubes can be use depending upon the area of the defect to be excised and sizes of 10, 15, 18, 20, 22, 25, 30 and 35 mm in diameter can be used. The distal end of the cylindrical sizing tube body 132 is formed with extending tri-pod legs or feet 134 with a sighting channel 136 running from the proximal end of the tube to the bottom of each foot 134 to form a sighting line for the surgeon. The sighting line 136 widens at 137 in each foot 134 to provide a marking pen slot 138 and a throughgoing aperture 139 is located at the distal end of the sizing tube and above the base of each foot 134 to provide a marking pen aperture and visualization port for viewing the defect area 200.

Figure 20:
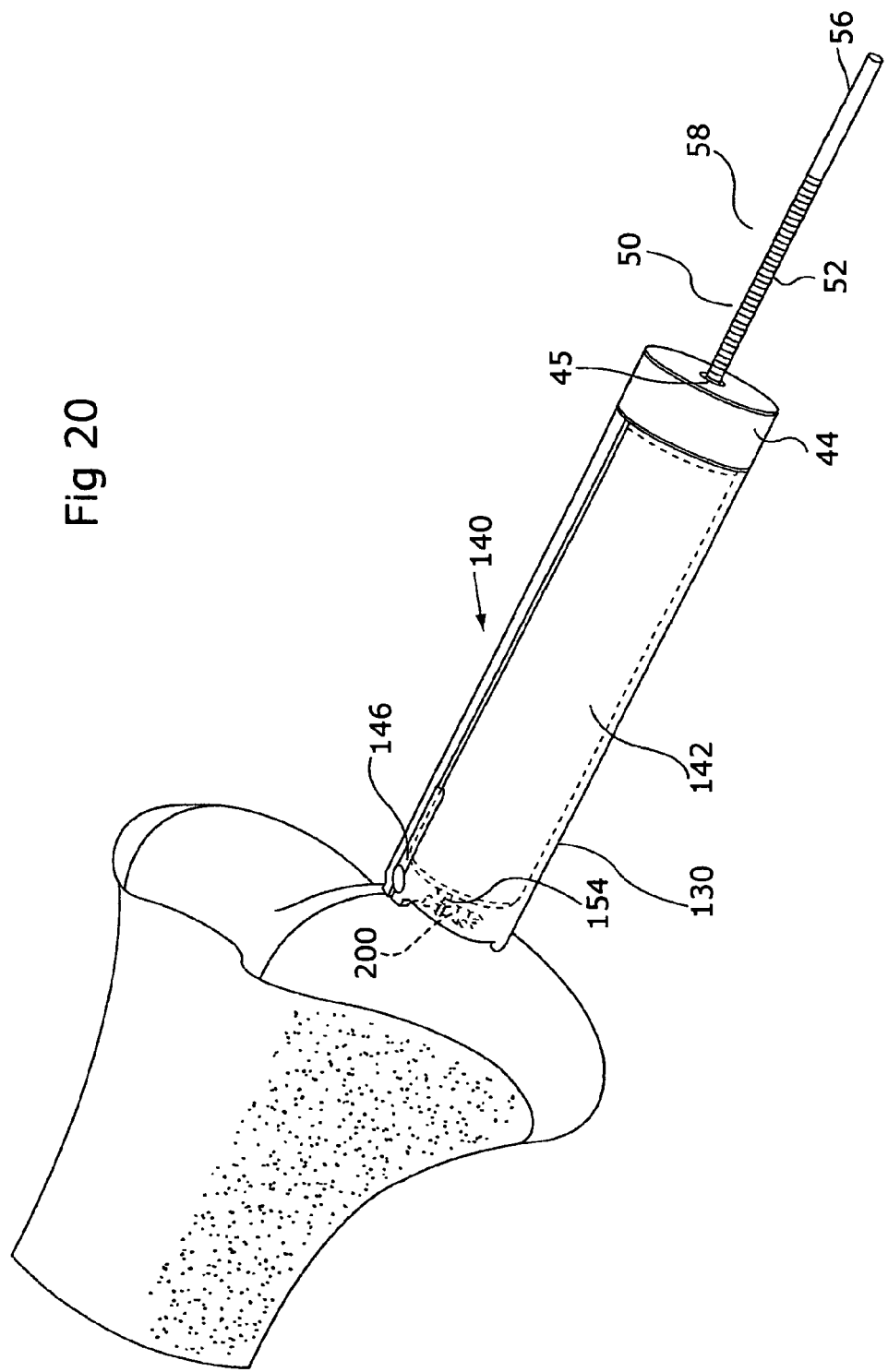
FIG. 20 is an enlarged perspective view of the drill centering guide member shown in FIG. 16 placed in the sizing tube with the drill guide rod located at the center of the defect.
Figure 21:
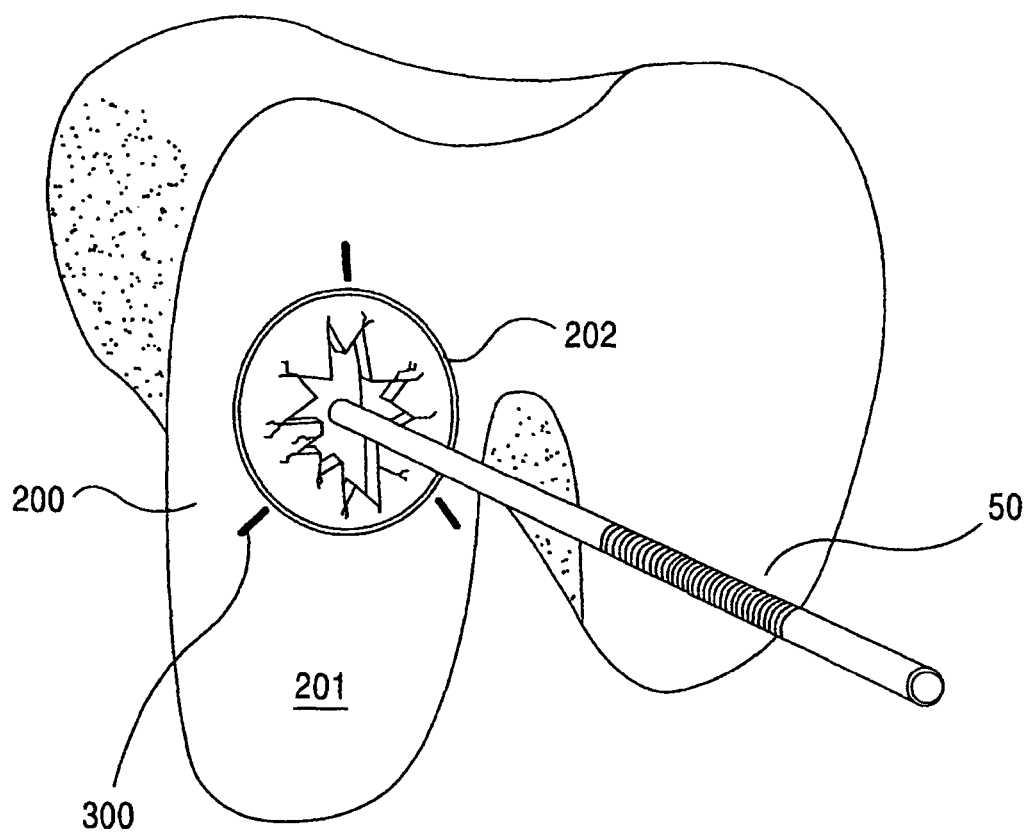
FIG. 21 is a perspective view of the drill guide rod in the condyle with the sizer and drill centering guide member removed.

A cannular guide rod centering tube 140 is then inserted in the sizing tube 130. As seen in FIG. 20, the guide rod centering tube 140 has been inserted into the sizing tube 130 for placement of the drill guide rod 50. The guide rod centering tube 140 is constructed with a metal cylindrical body 142 having an internally threaded cap 144 mounted over its proximal end, the cap 144 defining a centrally positioned aperture 145 which is sized to receive the guide drill rod 50. A planar end piece 146 as shown in phantom on FIG. 20 is mounted to the distal end of the cylindrical body 142, the end piece 146 also defining a centrally positioned aperture (not shown) which is axially aligned with aperture 145. If desired, a centrally positioned tube having an internal diameter which is greater than the outer diameter of the guide drill rod 50 can be concentrically mounted inside cylindrical body 142 to receive the guide drill rod 50.

Figure 22:
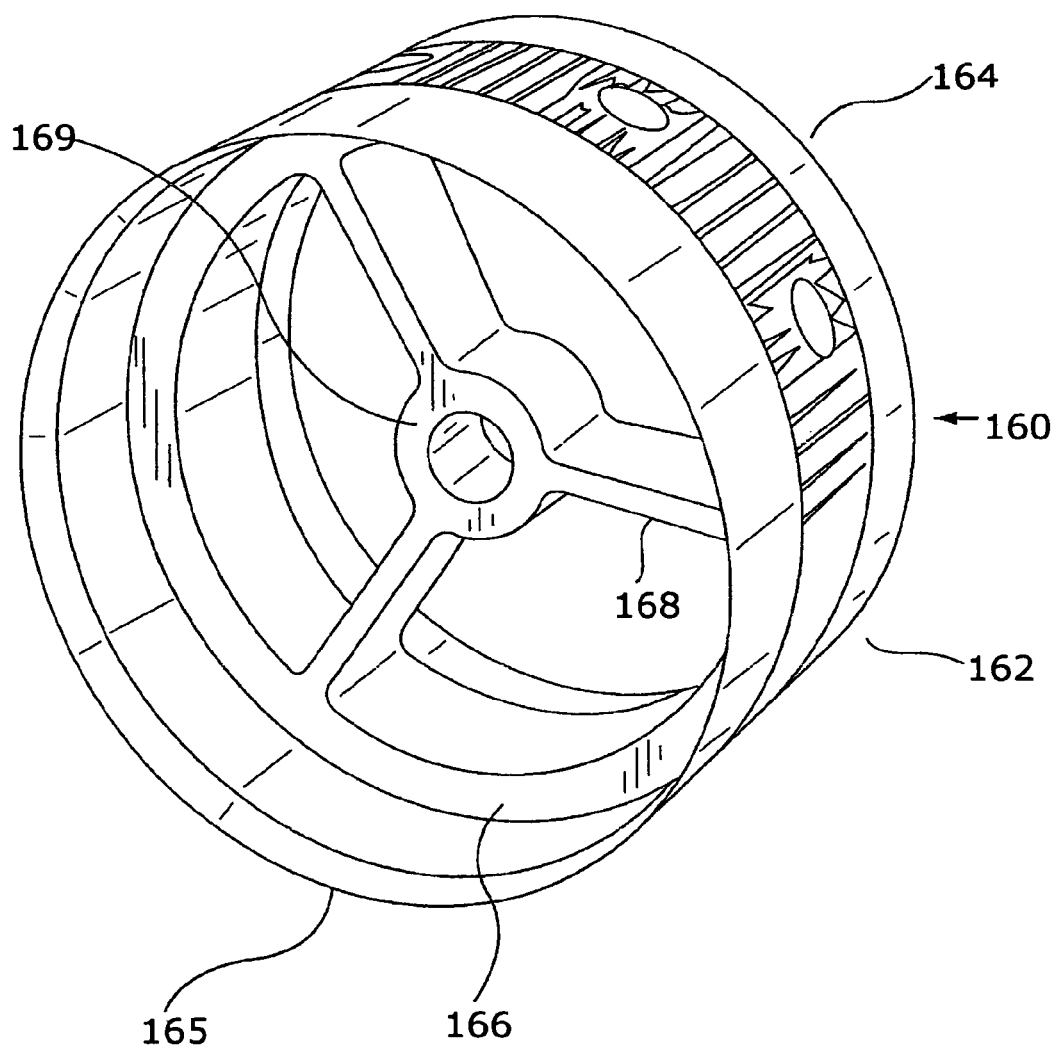
FIG. 22 is an enlarged perspective view of a punch cutter shown in FIG. 16 which can used for cutting the defect area of the cartilage on the condyle.
Figure 23:
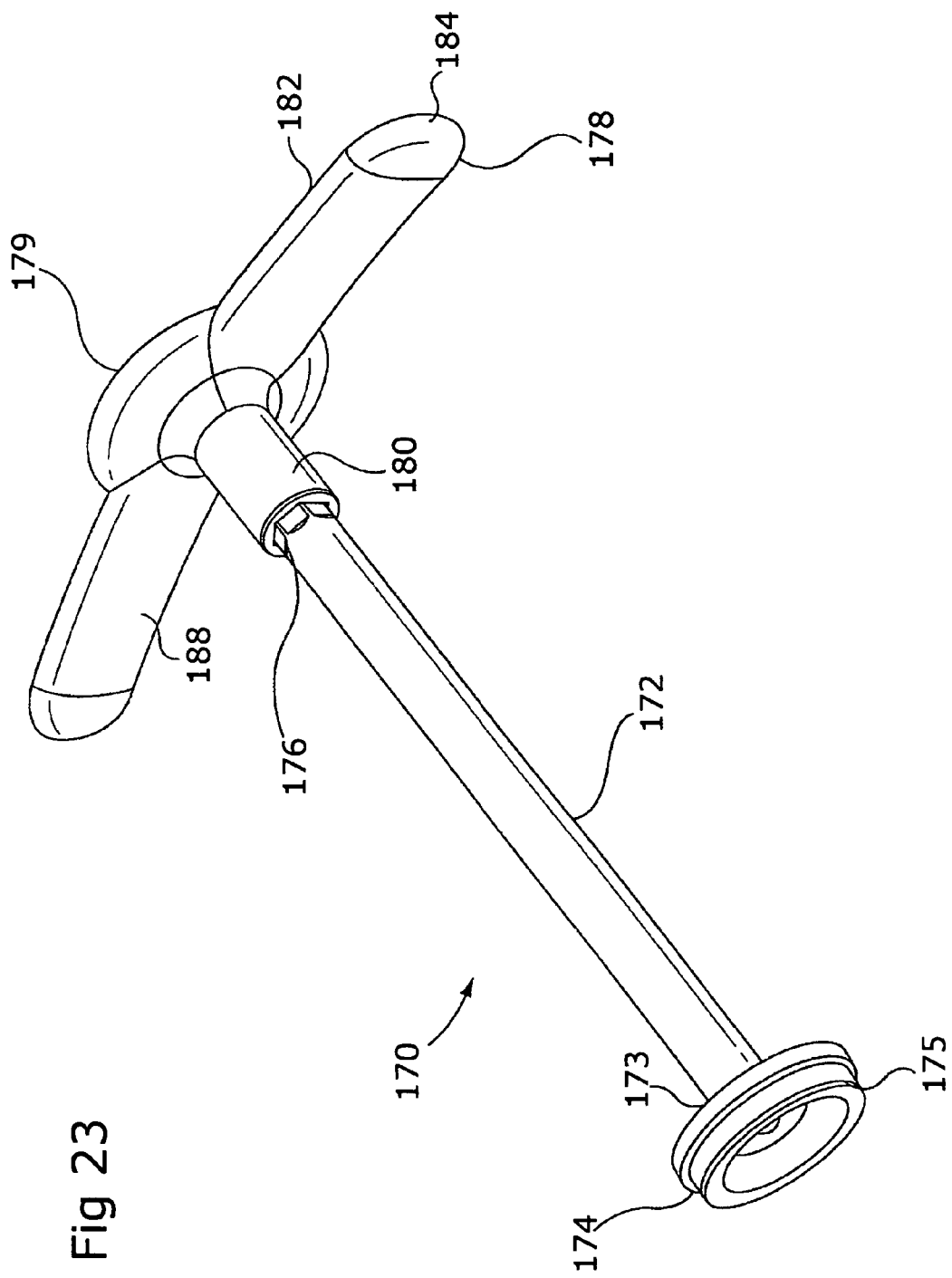
FIG. 23 is an enlarged perspective view of the T shaped removable drive handle shown in FIG. 16.
Figure 24:
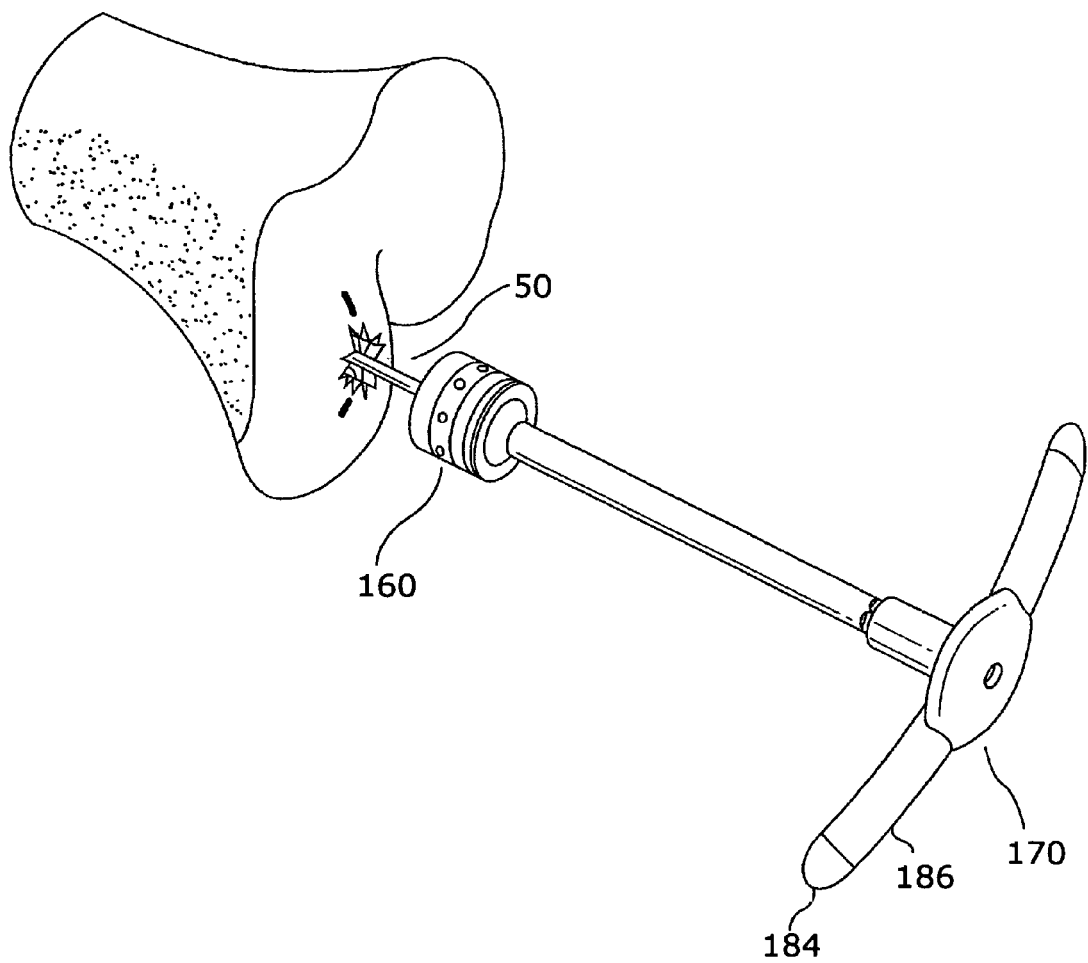
FIG. 24 is a perspective view of the T shaped drive handle of FIG. 23 with a mounted punch cutter of FIG. 22 mounted on the drill guide rod.

The guide rod centering tube 140 and sizing tube 130 are then removed from the guide drill rod 50 and a punch cutter 160 is threadably mounted to a cannular T-handle assembly 170. The punch cutter 160 shown in FIG. 22 has a cylindrical body 162 with a threaded collar 164 on the proximal end and a sharpened inwardly beveled distal cutting edge 165. A drill centering guide 166 is mounted inside the cylindrical body 162 and has a cylindrical outer body 167 with inwardly projecting arms or spokes 168 terminating in a circular hub 169 which serves as a drill centering guide when it is mounted over the guide drill rod 50. The punch cutter 160 is constructed of stainless steel and the drill centering guide 166 is preferably made of molded plastic with the total punch cutter 160 being a single use disposable item. The T-handle assembly 170 for the punch cutter is best seen in FIGS. 23 and 24 is constructed with interchangeable tubular shafts 172, the distal end 173 being secured to a threaded stepped collar 174 which receives the threaded collar 164 of the punch cutter 160 on its lower threaded section 175. The proximal end of shaft 172 has a quick release socket 176 which holds the removable handle 178 on the shaft. The handle 178 has a circular impact surface 179 with the top of the hammering surface being planar with a tubular section 180 which fits over the quick release socket 176. Arms 182 extend outward from the circular impact surface 179. The arms 182 are of a width and have curved ends 184. The top surface 186 and bottom surface 188 of the arms both have a curved surface which allows the same to be easily grasped by the user. If desired a punch cutter 160 and T-handle assembly 170 are mounted on the guide drill rod 50 as seen in FIG. 24 and the recipient punch cutter 160 is driven in by hand (straight and/or rotated) or hammered into the cartilage surface 201 of the patients condyle to cut a clean bore diameter in the patient recipient.

The T-handle assembly 170 and associated punch cutter 160 are removed from the drill rod 50 and the cannular boring bit 90 is mounted on the guide drill rod 50 against the scored area 202 of defect 200.

In operation, the lesion or defect is removed by cutting a blind bore 230 in a patient's bone of a predetermined diameter and depth in the defect area with a cannular boring bit 90. A lesion gauge 30 or sizing tube 130 is used to measure the extent of the defect 200 so that the defect is contained within the inner diameter of the lesion gauge 30 or sizing tube 130 and the cartilage defect area is marked 300 with a pen or other marking device to determine the orientation of the bore. When the alternate embodiment of FIG. 16 is used a drill rod centering guide 140 is inserted in the sizing tube 130.

The guide drill rod 50 is placed in the drill centering guide 140 or the bore 42 of the lesion gauge 30 against the defect 200 so that it is in the center of the defect area 200. Once the guide drill rod 50 is driven into the defect area and secured in the bone of the defect area, either the lesion gauge 30 or the sizing tube 130 and drill centering guide tube 140 are removed from the guide drill rod 50 leaving the guide drill rod 50 extending upward from the defect area 200. When the alternate embodiment of FIG. 16 is used a punch cutter 160 is threadably mounted to a cannular T-handle assembly 170 and mounted over the drill rod 50 so that the drill rod extends through the punch cutter hub 169 into the cannula of the T-handle assembly 50. The T-handle assembly 170 is driven with a hammer or other driving means so that the cartilage surface 201 of the defect area 200 is cut by the punch cutter leaving a clean cartilage cut without cracking or shattering. The associated punch cutter 160, blade 165 and T-handle assembly 170 is removed from the guide drill rod 50. With either embodiment the cannular reamer bit 90 which is selected in size to correspond to the diameter of the lesion gauge 30 or sizing tube 130 is mounted on the guide drill rod 50 and cuts out the defect area so that the rotating blade 94 cuts a blind bore 230 in the femur to remove the condyle defect 210 and associated cartilage 201 and bone 204. The result is a cleanly cut bore 230 as seen in FIG. 15 which is set to receive the cylindrical core of the allograft cartilage implant (not shown)

The length of the osteochondral plug implant can be the same as the depth of the bore 230 or less than the depth of the bore If the plug is the same length, the base of the plug implant is supported and the articular cartilage cap is level with the articular cartilage of the patients bone surface. If the plug is of a lesser length, the base of the plug implant is not supported but support is provided by the wall of the bore or respective cut out area as the plug is interference fit within the bore or cut out area with the cap being flush with the articular cartilage depending on the surgeon's preference. With such load bearing support the graft surface is not damaged by weight or bearing loads which can cause micromotion interfering with the graft interface producing fibrous tissue interfaces and subchondral cysts.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

The invention claimed is:

1. A surgical kit having component parts capable of use in excising a cartilage defect area of a patient to prepare the area for receipt of an implant plug, said kit comprising:
   a gauge apparatus used to measure the extent of the cartilage defect area and guide a guide rod, said gauge apparatus having a substantially cylindrical shaped body defining a central throughgoing bore of a diameter sufficient to receive said guide rod, a plurality of legs formed on said body extending away from the distal end of said tube body, a longitudinal marking line formed in at least one of said legs and an exterior surface of said gauge body;
   a guide rod adapted to be driven through said gauge apparatus bore into said defect area; and
   cartilage cutting means adapted to be mounted over said guide rod, said cartilage cutting means comprising a reamer bit defining a cannula adapted to be mounted over said guide rod for excising the defect area and cutting a blind cylindrical bore into a patient's condyle.

2. A surgical kit as claimed in claim 1 wherein said gauge body defines a plurality of longitudinal grooves formed on its exterior surface intersecting the midpoint of each of said legs, said longitudinal grooves forming sight lines for the person determining an area of the defect site.

3. A surgical kit as claimed in claim 1 wherein a distal end of said gauge body forms a conical recess leading into said central throughgoing bore.

4. A surgical kit as claimed in claim 1 wherein said gauge apparatus comprises a plurality of gauge members having different diameters.

5. A surgical kit as claimed in claim 4 wherein said gauge members diameters range from 10 mm to 35 mm.

6. A surgical kit as claimed in claim 4 wherein said gauge members are of different colors corresponding to the diameter of the gauge member.

7. A surgical kit as claimed in claim 1 wherein said central throughgoing bore is flared outward at its proximal end.

8. A surgical kit as claimed in claim 1 wherein said legs form a tripod on said body.

9. A surgical kit having component parts capable of use in excising a cartilage defect area of a patient to prepare the area for receipt of an implant plug, said kit comprising:
   a plurality of gauge guide members used to measure the defect area, each of said gauge guide members being provided with a throughgoing central bore adapted to receive a guide rod;
   a guide rod centering tube for insertion into a gauge guide member, said guide rod centering tube comprising a tubular body with a cap mounted over its proximal end, the cap defining a centrally positioned aperture which is sized to receive a guide rod and an end piece secured to the distal end of said tubular body, said end piece defining a centrally positioned aperture which is axially aligned with said cap aperture;
   a guide rod adapted to be driven through said bore of a selected gauge guide member into the center of said defect area; and
   cartilage cutting means comprising a plurality of reamer bits adapted to be mounted over said guide rod, each reamer bit defining a central cannula adapted to be mounted over said guide rod, a distal cutting surface for cutting a cylindrical blind bore into a patients cartilage and bone to excise the cartilage defect area and quick disconnect means on its proximal end.

10. A surgical kit as claimed in claim 9 wherein said drill bit has a shaft and a cutting head at its distal end, said cutting head being marked with depth markings.

11. A surgical kit having component parts capable of use in excising a cartilage defect site of a patient to prepare the same for receipt of an implant plug, said kit comprising:
   a gauge member used to measure the defect area and guide a guide rod; said gauge member comprising a body defining a central throughgoing bore, a plurality of legs secured to said body extending away from the distal end of said body, and a marking sight line formed on an exterior surface of at least one leg;

a guide rod adapted to be mounted in said gauge member body through going bore and driven into the center of said defect area; and cartilage cutting means adapted to be mounted over said guide rod, said cartilage cutting means comprising a cannular reamer bit adapted to be mounted over said guide rod for excising the defect area and cutting a blind cylindrical bore into a patients defect area, said reamer bit being constructed to score the outer diameter of the cartilage area before cutting into the defect area.

12. A surgical kit as claimed in claim 11 wherein said cartilage cutting means includes a cylindrical punch cutter member with insert means mounted inside said cylindrical punch cutter member, said insert means comprising a hub defining a central throughgoing bore, a plurality of arms extending outward from said hub and a cylindrical rim member mounted on the distal ends of said arms, said cylindrical rim member engaging an inner surface of said cylindrical punch cutter member.

13. A surgical kit as claimed in claim 11 wherein said gauge member is a sizing tube with a drill centering tube is inserted into said sizing tube, said drill centering tube comprising a tubular body with a threaded cap mounted over its proximal end, the cap defining a centrally positioned aperture which is sized to receive said drill rod and a planar end piece secured to the distal end of the cylindrical body, said end piece also defining a centrally positioned aperture which is axially aligned with the cap aperture.

14. A surgical kit as claimed in claim 11 wherein said reamer bit has a shaft and a cutting head at its distal end, said cutting head being marked with depth markings and having a cutting edge with a sharp angled leading edge, said cutting head defining angled channels running the length of the cutting head.

15. A surgical kit as claimed in claim 11 wherein said gauge member body has a first proximal cylindrical section, a tapered section leading to a smaller diameter cylindrical section and tripod legs extending from said smaller diameter cylindrical section.

16. A method of excising a cartilage defect area in a patient comprising the steps of:
a) marking the defect area to be cut with a cylindrical gauge defining a central throughgoing bore;
b) placing a guide rod through said central bore into the center of said defect area and driving the guide rod a predetermined distance in the defect area to secure the guide rod in the defect area; and
c) placing a reamer bit over the guide rod and rotating the reamer bit cut to cut a cylindrical blind bore removing the cartilage defect area.

17. A surgical kit having component parts capable of use in excising a cartilage defect area of a patient to prepare the area for receipt of an implant plug, said kit comprising;

a plurality of gauge guide members used to measure the defect area, each of said gauge guide members being provided with a throughgoing central bore adapted to receive a guide rod;

a guide rod adapted to be driven through said bore of a selected gauge guide member into the center of said defect area;

cartilage cutting means comprising a plurality of reamer bits adapted to be mounted over said guide rod, each reamer bit defining a central cannula adapted to be mounted over said guide rod, a distal cutting surface for cutting a cylindrical blind bore into a patients cartilage and bone to excise the cartilage defect area and quick disconnect means on its proximal end; and a punch cutter, said punch cuter comprising a cylindrical cutting tube, a distal end of said cutting tube forming a cutting edge and a proximal end of said cutting tube being formed with connection means, insert means mounted inside said cylindrical cutting tube, said insert means comprising a hub defining a central throughgoing bore, a plurality of arms extending outward from said hub and a cylindrical rim member mounted on the distal ends of said arms, an outer surface of said rim member engaging an inner surface of said cylindrical cutting tube when said insert means is mounted inside said cylindrical cutting tube.

18. A surgical kit having component parts capable of use in excising a cartilage defect area of a patient to prepare the area for receipt of an implant plug, said kit comprising;

a plurality of gauge guide members used to measure the defect area, each of said gauge guide members being provided with a throughgoing central bore adapted to receive a guide rod;

a guide rod adapted to be driven through said bore of a selected gauge guide member into the center of said defect area;

cartilage cutting means comprising a plurality of reamer bits adapted to be mounted over said guide rod, each reamer bit defining a central cannula adapted to be mounted over said guide rod, a distal cutting surface for cutting a cylindrical blind bore into a patients cartilage and bone to excise the cartilage defect area and quick disconnect means on its proximal end; and a handle assembly, said handle assembly comprising an impact member with a throughgoing bore, opposing arms extending from said impact member, a cylindrical tubular section secured to said impact member and axially aligned with said throughgoing bore, a shaft defining a cannula removably mounted at its proximal end to said tubular section and collar mounted to a distal end of said shaft.

19. A surgical kit as claimed in claim 18 wherein said collar is stepped and threaded and the proximal end of said shaft is provided with a quick disconnect socket.

20. A surgical kit as claimed in claim 18 wherein said impact member is circular and said arms have curved ends and curved bottom and upper surfaces.

* * * * *